(12) United States Patent
Rouw et al.

(10) Patent No.: US 7,738,951 B2
(45) Date of Patent: Jun. 15, 2010

(54) PRIORITIZED MULTICOMPLEXOR SENSING CIRCUIT

(75) Inventors: Mattias Rouw, Arnhem (NL); Patrick Scholten, Zutphen (NL)

(73) Assignee: Medtronic, Inc., Minneapolis, MN (US)

( * ) Notice: Subject to any disclaimer, the term of this patent is extended or adjusted under 35 U.S.C. 154(b) by 991 days.

(21) Appl. No.: 11/460,756

(22) Filed: Jul. 28, 2006

(65) Prior Publication Data

US 2008/0027342 A1 Jan. 31, 2008

(51) Int. Cl.
*A61B 5/04* (2006.01)

(52) U.S. Cl. .................................. 600/522

(58) Field of Classification Search ............ 600/439, 600/455, 522; 607/2, 3, 9, 14, 16, 18, 20, 607/59
See application file for complete search history.

(56) References Cited

U.S. PATENT DOCUMENTS

| | | | |
|---|---|---|---|
| 3,846,787 A | 11/1974 | Myers et al. | |
| 4,004,576 A | 1/1977 | Gahwiler et al. | |
| 4,533,994 A | 8/1985 | Harrill et al. | |
| 4,654,632 A | 3/1987 | Yoshida et al. | |
| 5,197,467 A * | 3/1993 | Steinhaus et al. | 607/20 |
| 5,617,090 A | 4/1997 | Ma et al. | |
| 6,310,571 B1 | 10/2001 | Yang et al. | |
| 6,556,859 B1 | 4/2003 | Wohlgemuth et al. | |
| 2003/0114888 A1 * | 6/2003 | Stadler et al. | 607/14 |
| 2003/0204140 A1 * | 10/2003 | Ferek-Patric et al. | 600/439 |
| 2003/0220673 A1 | 11/2003 | Snell | |
| 2005/0090756 A1 | 4/2005 | Wolf et al. | |
| 2008/0288023 A1 * | 11/2008 | John | 607/59 |

FOREIGN PATENT DOCUMENTS

| | | |
|---|---|---|
| EP | 0832600 A1 | 4/1998 |
| WO | 9413197 | 6/1994 |
| WO | 9633651 | 10/1996 |

* cited by examiner

*Primary Examiner*—George Manuel
*Assistant Examiner*—Robert N Wieland
(74) *Attorney, Agent, or Firm*—Stephen W. Bauer; Michael J. Ostrom

(57) ABSTRACT

An implantable medical device having a prioritized multiplexor sensing circuit used for monitoring the condition or status of a patient. The device includes patient parameter sensors, such as electrodes, that are monitored for indications of significant events. Sensors indicating the presence of significant events may then be monitored more often than the other sensors.

18 Claims, 9 Drawing Sheets

A AAA AAA AAA A    V VVV VVV VVV

PRIORITIZED MULTICOMPLEXOR SENSING CIRCUIT

BACKGROUND

The present invention relates generally to medical devices. In some embodiments, the invention relates generally to medical devices used for monitoring the condition or state of a patient.

Medical devices used for monitoring the condition or state of a patient may include diagnostic monitoring equipment, external medical device systems, implantable medical devices (IMDs), or combinations of such equipment, systems, and devices. As is known, IMDs can be used to monitor and/or treat patients suffering from a variety of conditions. Examples of cardiac IMDs may include implantable hemodynamic monitors (IHMs), implantable cardioverter-defibrillators (ICDs), cardiac pacemakers, cardiac resynchronization therapy (CRT) pacing devices, and drug delivery devices. Such IMDs are generally used to monitor the electrical activity of the heart, while some of the IMDs are also used to provide electrical stimulation to one or more of the heart chambers, when necessary.

IMDs generally utilize a plurality of electrodes and/or other sensors. In cardiac medical devices, for example, electrodes can be used to monitor the electrical condition and/or state of the patient. These electrodes are typically situated on one or more leads extending from such medical devices and positioned at corresponding locations within or proximate to the heart chamber. In use, the electrodes sense electrical signals within the cardiac tissue of the heart, and subsequently pass analog signals (e.g., corresponding to the sensed electrical signals) back to the medical devices. Within the medical devices, these analog signals are typically converted to digital signals, which are, in turn, stored within memory of the devices or transmitted to further devices having memory. As is known, for each electrode or other sensor which transfers analog signals corresponding to a cardiac parameter, one or more electrical components are located within the medical device in order to digitize the analog signals and/or condition such transmitted signals prior to their storage. In devices designed to subsequently provide therapy when necessary, such digitized signals are analyzed, e.g., by a controller within the device, so as to provide the appropriate therapy from the device.

What is needed are medical devices which enable the above-described general monitoring functionality, yet have more efficient designs. In turn, such devices may be less expensive to build. In addition, by making the devices more efficient, less space within the devices may be required in providing the above-described general functioning. As a result, the devices can be made more compact in size, or alternatively, such excess space can be further used in making the devices more versatile in their overall functioning.

DETAILED DESCRIPTION

Figure 1:
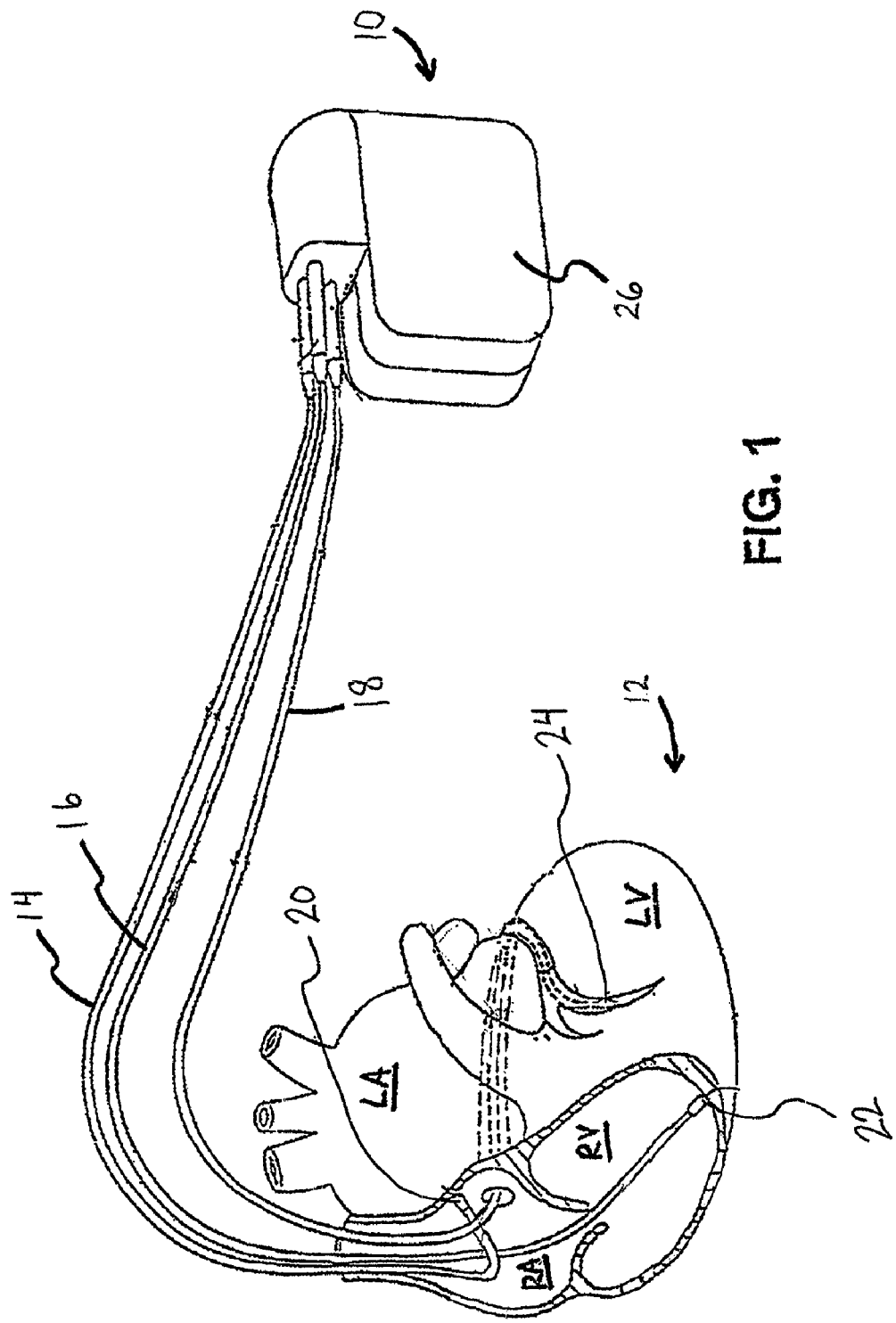
FIG. 1 is a schematic representation of an exemplary medical device 10 that can be used in accordance with embodiments of the invention.

The following detailed description should be read with reference to the drawings, in which like elements in different drawings are numbered identically. The drawings depict selected embodiments and are not intended to limit the scope of the invention. It will be understood that embodiments shown in the drawings and described below are merely for illustrative purposes, and are not intended to limit the scope of the invention as defined in the claims.

Generally, in a medical device used for monitoring the condition or status of a patient, efficiency is one concern. In some instances, this can involve designing new medical devices that provide the same functionality as previous devices, but with fewer electronic components. By reducing the quantity of electronic components within a medical device, the cost of producing the device can be reduced. In addition, overall energy consumption of the device can often be reduced. Further, in some cases, as suggested above, the size (e.g., volume and/or mass) of the device can be reduced. As a result, many further advantages can be realized by maintaining present functionality but using fewer electronic components.

Medical devices used for monitoring a patient's condition and/or status each encase a controller (e.g., a microprocessor) that is used to provide a plurality of functions. As a consequence of increasing a medical device's efficiency, other advantages can likely be realized with respect to such controller. For example, if the medical device is designed with fewer electronic components which normally function either on or with the controller, the space on the controller usually dedicated for such would be freed up to be used elsewhere. As such, the controller can be made more versatile so as to provide further functioning for the device. Alternatively, the controller could be downsized, which in turn, could lead to a reduction in size of the medical device.

Certain embodiments of the invention involve medical devices used for monitoring the condition and/or status of a patient. As described above, such medical devices generally include a plurality of electrodes and/or other sensors used for such monitoring purposes, with such electrodes and other sensors each being electrically connected to electrical components housed within the medical device. One such electrical component may include an analog-to-digital converter (ADC). The function of an ADC is to digitize its analog signal inputs. For example, with respect to cardiac medical devices, electrodes placed in contact or proximate to certain heart regions would be used to sense cardiac electrical activity in such regions. In turn, the electrodes would transfer analog signals (corresponding to the sensed cardiac electrical activity) to an ADC within the medical device (e.g., via the electrode leads). Another electrical component may involve a sense amplifier circuit. Typically, such sense amplifier circuits can be used to condition incoming signals, prior to or after their digitization. As a result, the incoming signals can be adjusted to a form that enables more effective interpretation of the signals, and in turn, leads to more effective treatments being prescribed for the patient.

As is well known, such ADCs and/or sense amplifier circuits take up valuable space within the medical device. As described above, current medical devices generally utilize electrodes and/or other sensors for monitoring purposes. Significant varieties of information can be gathered from the patient through the use of such large quantities of electrodes and/or other sensors. However, such medical device configurations also generally necessitate an ADC, and optionally, a sense amplifier circuit, being used within the device for each electrode and/or other sensor for reasons described above. It has been found that including such quantities of ADCs and optional sense amplifier circuits has a negative impact, not only on the medical device size, but also on efforts to increase the overall versatility of the medical device.

Certain embodiments of the invention provide a medical device with a limited quantity of ADCs and optional sense amplifier circuits in comparison to current medical device designs, while still employing the same quantities of electrodes and/or other sensors normally utilized with such current medical devices.

As will be further described and illustrated below, in certain embodiments, a medical device is provided including only a single ADC and optionally, a single sense amplifier circuit, to interact with the device's electrodes and/or one or more other sensors of the device. In certain embodiments, by utilizing a multiplexor (MUX) and a demultiplexor (DE-MUX), in combination with such above-mentioned single ADC and optional single sense amplifier circuit, a system is provided in which channels carrying signals from the electrodes and/or other sensors can be alternately monitored, during which times corresponding signals are sampled. In certain embodiments, upon each sampling, the corresponding signal is output to the ADC and optional sense amplifier circuit. A "normal mode" of operation of the system involves the MUX sending each of the sampled signals in generally equal time increments. When a signal carried across one of these channels is interpreted as involving a significant event (e.g., when a signal provides statistically significant data or when a patient's condition may appear to be compromised), the corresponding channel is designated as high priority and the system is switched to a "high priority mode" of operation. In turn, over a preset time period, all the channels can still be alternately monitored. However, during such preset time period, the high priority channel is monitored for longer time increments as opposed to when such channel was monitored during the "normal mode" operation of the system.

The system of such embodiments is designed to enable alternative monitoring of a plurality of channels via a single ADC and optional sense amplifier circuit regardless of the system's operating mode. However, by being configured to assign high priority status to certain channels based on the presence of an event, the system can, in turn, increase the resolution of such high priority channel. As a result, the event sensed across such channel can be sufficiently captured by the device and in turn, be used for providing immediate treatment to the patient or be used in the future for diagnosing the condition of the patient.

FIG. 1 shows a schematic representation of an exemplary medical device 10 that can be used in accordance with certain embodiments of the invention. As shown, the medical device 10 is an IMD; however, the invention should not be limited to any particular IMD, or to any medical device. Instead, any medical device could be utilized in embodiments of the invention so long as such device utilizes a plurality of electrodes or other sensors which pass signals along to the device for patient monitoring purposes. Further, in embodiments in which cardiac medical devices are utilized, the medical device 10 can be any device that is, via the use of electrodes or other sensors, capable of measuring hemodynamic parameters (e.g., blood pressure signals) from within a patient's heart and/or which is capable of measuring other cardiac parameters or signals, such as the patient's electrogram (EGM).

In FIG. 1, heart 12 includes the right atrium (RA), left atrium (LA), right ventricle (RV), left ventricle (LV), and the coronary sinus extending from an opening in the right atrium into the great vein.

FIG. 1 schematically depicts the medical device 10 in relation to the heart 12. In certain embodiments, the medical device 10 may be an implantable, multi-channel cardiac pacemaker. As shown, three endocardial leads 14, 16, and 18 connect the medical device 10 with the RA, the RV and the LV, respectively. Each lead includes at least one electrical conductor and pace/sense electrode. For example, leads 14, 16 and 18 are respectively connected to pace/sense electrodes 20, 22, and 24. In addition, a can electrode 26 may be formed as part of the outer surface of the housing of the medical device 10. The pace/sense electrodes 20, 22, and 24 and can electrode 26 may be selectively employed to provide a number of unipolar and bipolar pace/sense electrode combinations for pacing and sensing functions. The depicted positions in or about the right and left heart chambers are merely exemplary. Moreover, other leads and pace/sense electrodes may be used instead of, or in combination with, any one or more of the depicted leads and electrodes.

Typically, in systems of the type illustrated in FIG. 1, the electrodes designated above as "pace/sense" electrodes are used for both pacing and sensing functions. In certain embodiments, the pace/sense electrodes can be used in programmed combinations for sensing cardiac signals and delivering pace pulses along pacing and sensing vectors. Alternatively, one or more of such pace/sense electrodes can be selected to be used exclusively as sense electrodes.

In addition, some or all of the leads 14, 16, and 20 shown in FIG. 1 could carry one or more pressure sensors for monitoring systolic and diastolic pressures, and/or a series of spaced apart impedance sensing leads for developing volumetric measurements of the expansion and contraction of the RA, LA, RV and LV. As described above, such pressure sensors and/or impedance sensing leads include examples of the many other sensors that could also be used for monitoring purposes (as opposed to or in combination with the pace/sense electrodes illustrated in FIG. 1) in embodiments of the invention. Further examples of the other sensors may include accelerometers, flow probes, microphones, sonometric crystals, metabolic or chemical sensors, and any electrical and/or mechanical sensors.

The leads and circuitry described above can be employed to record a plurality of cardiac parameters, e.g., EGM signals, blood pressure signals, and impedance values, over certain time intervals. The recorded data may be periodically telemetered out to a programmer operated by a physician or other healthcare worker in an uplink telemetry transmission during a telemetry session, for example.

Figure 2:
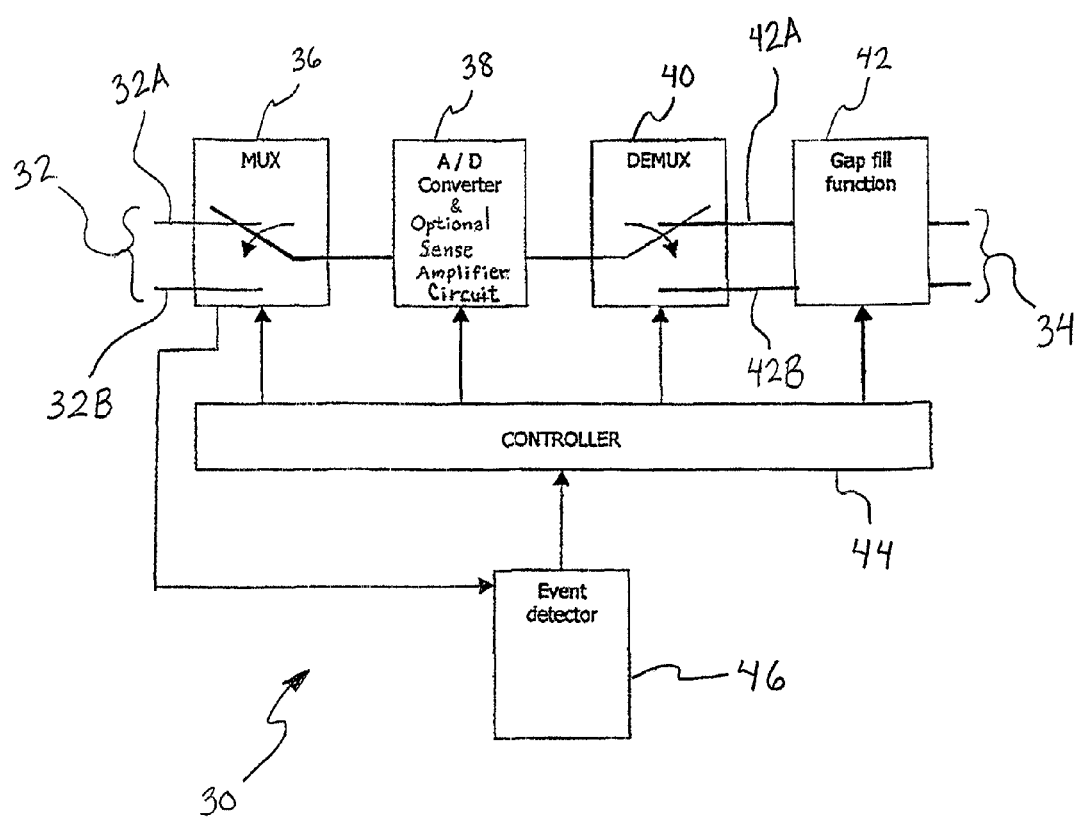
FIG. 2 is an exemplary block diagram of a system in accordance with embodiments of the invention.

FIG. 2 illustrates an exemplary block diagram of a system in accordance with certain embodiments of the invention. The system 30 is generally housed within a medical device, e.g., such as medical device 10 of FIG. 1. As shown, the system 30 has a plurality of input channels 32 and a corresponding plurality of output channels 34. While the input channels 32 and corresponding output channels 34 shown each involve two channels, the invention is not be limited to such. Instead, embodiments of the system 30 can include any number of input channels 32 and output channels 34, where that number corresponds to the number of electrodes and/or other sensors employed by the medical device. For example, with respect to the medical device 10 exemplified in FIG. 1, a system in accordance with certain embodiments of the invention may include four pairs of input channels and output channels, with each input and output channel pairing corresponding to one of the four electrodes 20, 22, 24, and 26 of the medical device 10. In turn, such electrodes 20, 22, 24, and 26 would be respectively connected to the four input channels of such system, via the leads (e.g., 14, 16, or 18) and via connection to the medical device can.

In certain embodiments, as illustrated, located between the input channels 32 and output channels 34 are electrical components including a mutiplexor (MUX) 36, an analog-to-digital converter (ADC) 38, a demultiplexor (DEMUX) 40, gap-fill function circuitry 42, a controller 44, and an event detector 46. In certain embodiments, the ADC 38 would also include a sense amplifier circuit, electrically connected before or after the ADC 38.

Figure 3:
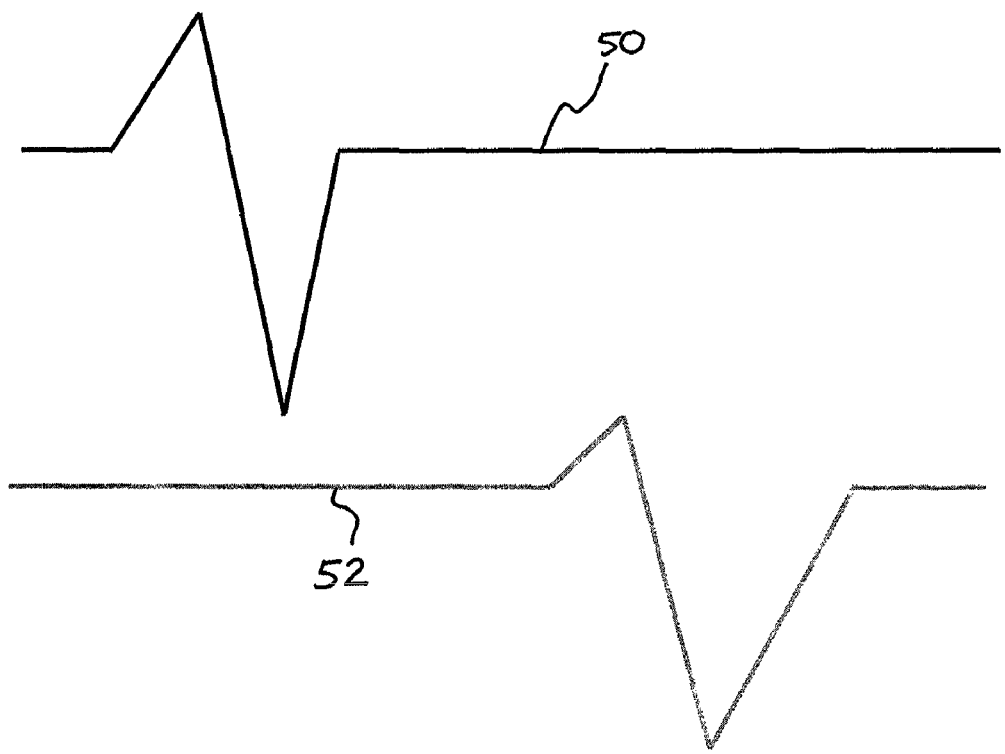
FIG. 3 is a representation of exemplary analog signals respectively transmitted by two electrodes and/or sensors to the system of FIG. 2.

As described above, cardiac parameters sensed by electrodes and/or other sensors would be passed in the form of analog signals to the medical device. As further described above, each of the input channels 32 of the system 30 would be electrically connected between one of the electrodes or one of the other sensors and the MUX 36 of the system 30. FIG. 3 shows exemplary analog signals respectively transmitted by two such electrodes and/or sensors to the system of 30. In certain embodiments, the two signals 50, 52 may correspond to distinct cardiac parameters being sensed from a patient's heart; as shown, such signals 50 and 52 respectively represent an atrial parameter and a ventricular parameter of the patient's heart. However, it should be appreciated the invention should not be limited as such. Instead, as described above, the system could include any medical device used for monitoring purposes, cardiac or otherwise.

As is known, the MUX 36 is a communications device that combines several signals for transmission over a single medium. The MUX 36 is powered by the controller 44 and, in certain embodiments, is configured to operate according to one or more switching rates, or frequencies, alternatively switching between each of the different input channels 32 at such switching rates. In certain embodiments, the controller 44 is pre-programmed to control the switching rates of the MUX 36. As can be appreciated, an initial switching rate of the MUX 36 must be set appropriately so as to prevent the possibility of events being missed by the system 30. For example, with respect to cardiac medical devices, arrhythmic events generally occur within the atrium at a much faster rate than events occurring within the ventricles. As such, in certain embodiments involving cardiac medical devices, when cardiac parameters are alternatively sampled from both the atrium and ventricles by the system 30, the initial switching rate would generally be set at a higher frequency than what would be needed when cardiac parameters are sampled from the ventricles only.

As described above, during MUX 36 operation, each input channel, e.g., 32A and 32B, is monitored in an alternating manner. Using the system 30 shown in FIG. 2 as an example, the MUX 36 would switch between the input channels 32A and 32B at a certain initial sampling rate. During the times when the MUX 36 is positioned at any of the input channels 32, the MUX 36 would sample signals across such channels. In certain embodiments, under a "normal mode" of operation, each time period in which the MUX 36 is positioned at any one input channel, e.g., 32A, would generally be equal to the time period in which the MUX 36 is positioned at the other input channels, e.g., 32B. Therefore, with respect to FIG. 2, for each sampling cycle of the MUX 36 under a "normal mode" or a "first mode" of operation, the input channels 32A and 32B would be sampled at a 1:1 ratio.

Upon being sent to the MUX 36, the sampled signals for each of the input channels 32A and 32B are in turn also fed to the event detector 46. The event detector 46, in turn, makes a determination as to whether the sampled signal meets one or more criteria. If the one or more criteria are not met, the system 30 would remain in the "normal mode" of operation, with the MUX 36 functioning as described above. However, if the sampled signal is found to meet the one or more criteria, this finding would be an indication that an event is occurring (e.g., that significant information exists on the sensor channel or a patient's condition is or may appear to be compromised). In such case, a signal is sent from the event detector 46 to the controller 44. The controller 44, in turn, would switch the system 30 over to a "high priority mode" or "second mode" of operation.

Under such "high priority mode" of operation, the input channel, from which a sampled signal was found to meet the one or more criteria, would be designated as a high priority channel. In turn, during a preset time period, all the channels may still be alternately monitored. However, during such preset time period, the high priority channel is monitored for longer time increments as opposed to when such channel was monitored during the "normal mode" operation of the system. In addition, if the channels carrying signals from the other electrodes or other sensors are also monitored in the "high priority mode", such channels would still be monitored over time increments used in the "normal mode" of operation. As such, in certain embodiments, the input channels 32A and 32B would be respectively sampled at a different ratio (further described below) as opposed to the 1:1 sampling ratio described above with respect to the "normal mode" of operation.

Figure 4:
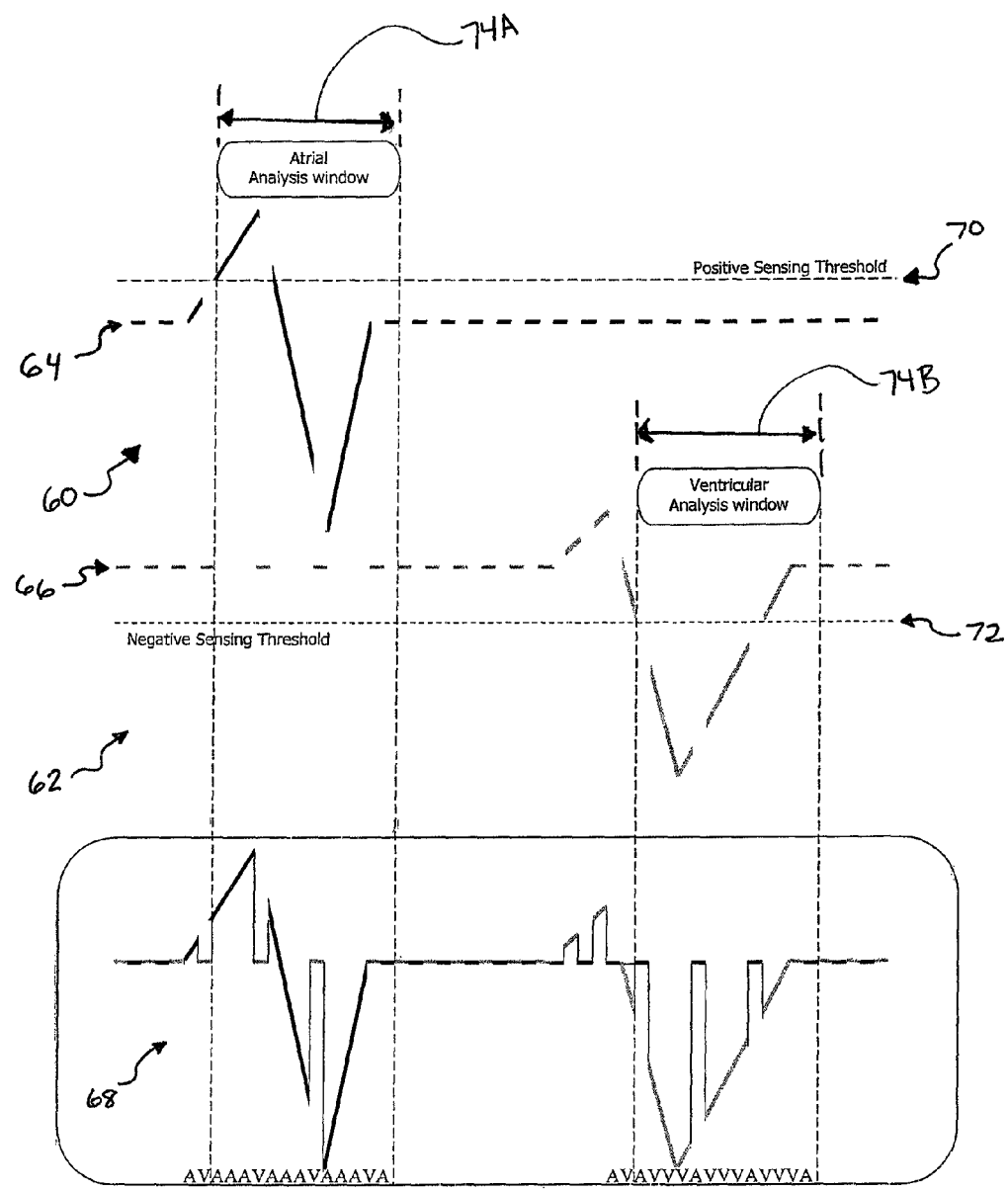
FIG. 4 illustrates an exemplary series of timelines depicting the sampling of the analog signals of FIG. 3 by a MUX of the system of FIG. 2.

FIG. 4 illustrates an exemplary series of timelines depicting the sampling of analog signals derived from certain input channels of the system 30 of FIG. 2. Using FIGS. 2 and 3 as a reference, signals 50 and 52 are respectively sampled from the input channels 32A and 32B in an alternative manner by the MUX 36. The alternate sampling of such signals 50 and 52 is respectively represented on a first timeline 60 as sampled signal 64 and on a second timeline 62 as sampled signal 66. In addition, a third timeline 68 illustrates the output of the MUX 36, showing a combination of sampled signals 64 and 66.

The first and second timelines 60, 62 help illustrate how the MUX 36 functions in "normal mode" and "high priority mode" with respect to the two input channels 32A, 32B of the system 30. As shown and described above, the system 30 initially operates in a "normal mode", whereby the MUX 36 alternately monitors each input channel, e.g., 32A and 32B, at a 1:1 ratio, as described above. In turn, as shown in FIG. 4 and with reference to FIGS. 2 and 3, each of the signals 50 and 52 is alternately sampled with respect to the 1:1 ratio from each of the channels 32A and 32B, respectively. This is further shown at the lower footer of the third timeline 68, where samplings shown in timelines 60 and 62 are respectively represented by "A" (atrial) and "V" (ventricular) sampling designations. As shown in such lower footer, the ratio of such "A" to "V" samplings is initially 1:1.

As described above, during each signal sampling, the event detector 46 is fed such sampled signal information in order to make a determination as to whether the sampled signal meets one or more criteria. As exemplified in FIG. 4, in certain embodiments, such one or more criteria may involve threshold values. In certain embodiments, as shown, the one or more criteria may be different for each input channel. For example, as exemplified in FIG. 4, while the one or more criteria both involve thresholds for each of the sampled signals, the threshold for the sampled signal 64 involves a positive threshold 70, while the threshold for the sampled signal 66 involves a negative threshold 72. It should be appreciated that a wide variety of criteria may be used by the event detector 46 to interpret the sampled signals and the use of thresholds as described herein are only provided for exemplary purposes.

As described above, if the sampled signals are not found to meet the one or more criteria, the system 30 continues to operate in the "normal mode", whereby, in certain embodiments, the MUX 36 continues to alternatively monitor the input channels 32 and sample the signals carried by such channels at a 1:1 ratio. However, as described above, if one of the sampled signals carried across the corresponding channels is found to meet the one or more criteria, the event detector 46 communicates such to the controller 44. In turn, the controller 44 designates the corresponding channel as high priority and switches the operation of the system 30 to a "high priority mode" for certain preset durations, e.g., with such preset durations being timed out by the controller 44 from the last occurring threshold crossing.

During such "high priority mode", the controller 44 alters the sampling rate at which the MUX 36 operates. In particular, the sampling rate is modified so that the high priority channel can be sampled for longer periods of time over each sampling cycle of the MUX 36 during the pre-set durations. As a result, during such pre-set durations, the sampling ratio of the MUX 36 with respect to the input channels 32 of the system 30 is also altered with respect to such high priority channel. For example, in certain embodiments as shown in FIG. 4, once the sampled signal 64 of timeline 60 is found to meet the one or more criteria (e.g., being at or extending beyond the positive threshold 70), the sampling ratio for the MUX 36 is changed to 3:1 for each sampling cycle during a preset duration 74A. In turn, for each sampling cycle over duration 74A, the MUX 36 samples the signal 50 carried by the high priority channel for a time period three times longer than when such signal 50 was sampled during "normal mode" operation. In certain embodiments, for each sampling cycle over duration 74A, the signal carried by the other channel, e.g., signal 52, is also sampled, but only for time periods at which such signal was sampled during "normal mode" operation. Again, this is shown in the lower footer of the third timeline 68. As shown, the ratio of "A" to "V" samplings over preset duration 74A is generally 3:1.

As further illustrated in FIG. 4, the sampled signal 66 of the timeline 62 is also found to meet the one or more criteria (e.g., being at or extending beyond the negative threshold 72). As a result, the sampling ratio for the MUX 36 is changed to 3:1 for each sampling cycle during preset duration 74B. In turn, for each sampling cycle over duration 74B, the MUX 36 samples the signal 52 carried by the high priority channel for a time period three times longer than when such signal 52 was sampled during "normal mode" operation. In certain embodiments, for each sampling cycle over duration 74B, the signal carried by the other channel, e.g., signal 50, is also sampled, but only for time periods at which such signal was sampled during "normal mode" operation. Again, this is shown in the lower footer of the third timeline 68. As shown, the ratio of "V" to "A" samplings over preset duration 74B is generally 3:1.

As should be appreciated, the 3:1 ratio described above and illustrated with respect to FIG. 4 is generally exemplary, and can be modified as desired, so long as the high priority channel is monitored for extended lengths in comparison to the other channels. As can be appreciated, such ratio can be N:1, where N>1. Alternatively, in certain embodiments, such ratio could be N:1:N, where N involves sampling time periods for signals sampled from the high priority channel and can be 1 or higher. By being configured to assign high priority status to such channels based on the sampled signal meeting one or more criteria (indicating the presence of an event), the system can, in turn, increase the resolution of such high priority channel. In addition, during "high priority mode" operation of the system 30, while the sampling cycles of the MUX 36 are described above and illustrated with reference to FIGS. 2 and 4 so as to include all channels, it should be appreciated that, in certain embodiments, such sampling cycles can be set so as to only include monitoring of the high priority channel.

Generally, as described above, when a signal carried across a channel is found to meet the one or more criteria, the system 30 is configured to extend monitoring of that channel, and in turn, sampling of that signal for increased durations per sampling cycle. However, in cases where two or more signals respectively carried across two or more channels are found to meet the one or more criteria at the same time, the system 30 would be configured to prioritize these channels accordingly (e.g., via the controller 44). In turn, only one of these channels would be designated high priority; however, this designation would occur so that the most critical signal is given priority. For example, this situation may present itself in cardiac medical devices where signals from both the atrium and ventricles are monitored by the system 30. If signals from one of the atrium and from one of the ventricles were both found to meet the one or more criteria, in certain embodiments, the controller 44 of the system 30 would be configured to give priority to one of the signals. Since ventricular events are generally considered more life-threatening than atrial events, the controller 44 in such exemplary cases, may be configured to give priority to the ventricular signals, thereby designating the corresponding ventricular channel as high priority, with increased monitoring of such channel during durations as described above.

Figure 5:
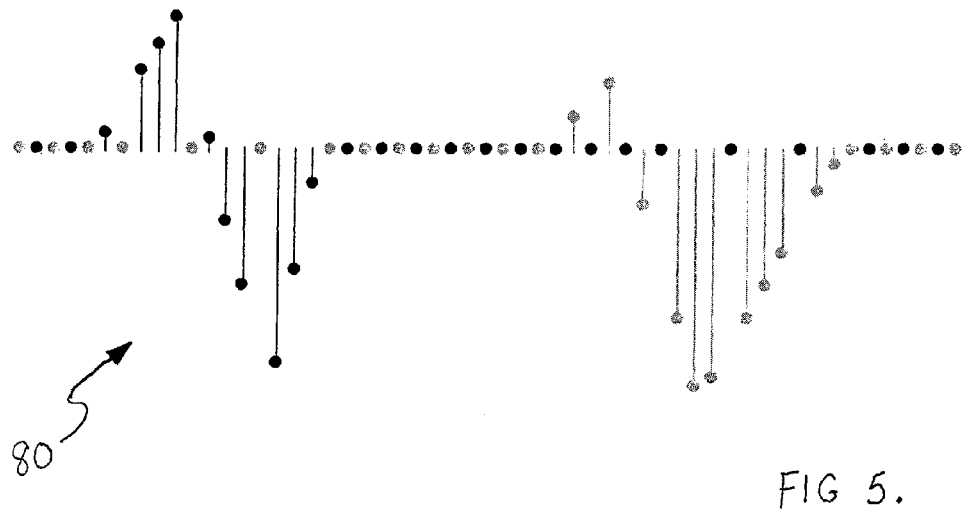
FIG. 5 illustrates an exemplary timeline depicting an output of an ADC of the system of FIG. 2 based on an input to the ADC of combined sampled signals shown on a timeline of FIG. 4.

Referring back to FIG. 2, the analog signals for each input channel 32A and 32B alternatively sampled by the MUX 36 would each in turn be fed into the ADC 38. Such ADC 38 is powered by the controller 44. As described above, the ADC 38 would digitize each analog signal passed therethrough. Regardless of the operating mode of the system, it should be appreciated from FIG. 2 and the above description that the ADC 38 would only be receiving, and in turn, digitizing one analog signal at a time because of the use of the MUX 36. It should be further appreciated that during "normal mode" operation of the system 30, the signals received by the ADC 38 would generally have equal time period (corresponding to the 1:1 sampling ratio of the MUX 36). Conversely, during "high priority mode" of the system 30, the signals received by the ADC 38 would generally have distinct time periods (corresponding to the altered sampling ratio of the MUX 36, exemplified above with reference to FIG. 4 as 3:1). FIG. 5 illustrates an exemplary timeline 80 depicting an output of the ADC 38 based on an input to ADC 38 of combined sampled signals 64 and 66 shown on timeline 68 of FIG. 4.

As described above, in certain embodiments, the ADC 38 can also include sense amplifier circuit 48, which would also be powered by the controller 44; however, the invention should not be limited to such. It should be appreciated that medical devices are generally designed with regard to conditioning the input signals via the use of a sense amplifier circuit; however, some medical devices may designed without such circuitry and these devices would still fall within embodiments of the invention. Further, even if medical devices are designed having signal conditioning via the use of a sense amplifier circuit; it should be appreciated that such signal conditioning could occur outside the system 30 as well and still fall within embodiments of the invention. As such, while inclusion of the sense amplifier circuit 48 at the same stage of the ADC 38 is often provided, such is optional with respect to the embodiments of the invention.

The output of the ADC 38 would be fed into the DEMUX 40. As is known, DEMUX 40 is a communications device generally used with a multiplexor to separate multiplexed or combined signals from a single medium. The DEMUX 40 is powered by the controller 44 and is configured to operate according to a certain switching rate, or frequency, alternatively switching between each of separate inputs of the gap-fill function circuitry 42. It should be appreciated that the number of inputs of the gap-fill function circuitry 42 would correspond with the number of inputs 32 of the system 30.

Figure 6:
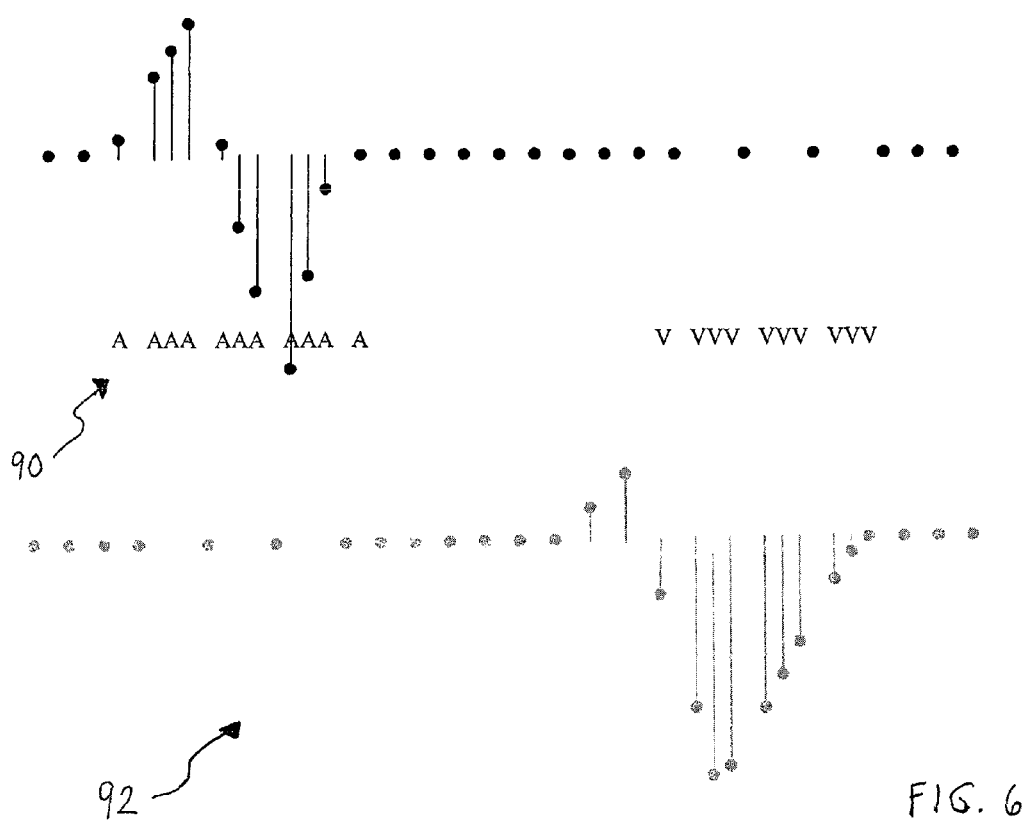
FIG. 6 illustrates an exemplary series of timelines depicting outputs of a DEMUX of the system of FIG. 2 based on an input to the DEMUX of signal shown on the timeline of FIG. 5.

In certain embodiments, the controller 44 is pre-programmed to control the switching rate of the DEMUX 40. As should be appreciated, both the MUX 36 and DEMUX 40 would be controlled by the controller 44 to have the same sampling rates, or frequencies. As such, when the sampling rate for the MUX 36 is altered when the system 30 is switched in operation from "normal mode" to "high priority mode" or vice versa, the controller 44 would likewise alter the DEMUX 36 sampling rate. In addition, both the MUX 36 and DEMUX 40 would be switched at identical times with respect to another. As such, the system 30 would form a closed circuit when sampling of a signal occurs. Further, only one signal would be sampled by the system 30 at any given time. For example, referencing FIG. 2, the MUX 36 would connect with one of the inputs, e.g., 32A, at the same time the DEMUX 40 closes with an input, e.g., 42A, of the gap-fill function circuitry 42. The corresponding analog signal of the connected input channel 32A sampled by the MUX 36 would be digitized by the ADC 38, with such digitized signal being passed to the DEMUX 40 and further output to the gap-fill function circuitry input 42A. Both the MUX 36 and the DEMUX 40, operating at the same switching rate, would subsequently switch at the same time to the other input 32B and other input 42B of the gap-fill function circuitry 42, respectively. In turn, the corresponding analog signal of the connected input channel 32B sampled by the MUX 36 would be digitized by the ADC 38, with such digitized signal being passed to the DEMUX 40 and further output to the gap-fill function circuitry input 42B. FIG. 6 shows exemplary timelines 90 and 92 depicting outputs of the DEMUX 38 based on an input to the DEMUX 38 of signal shown on timeline 80 of FIG. 5.

Figure 7:
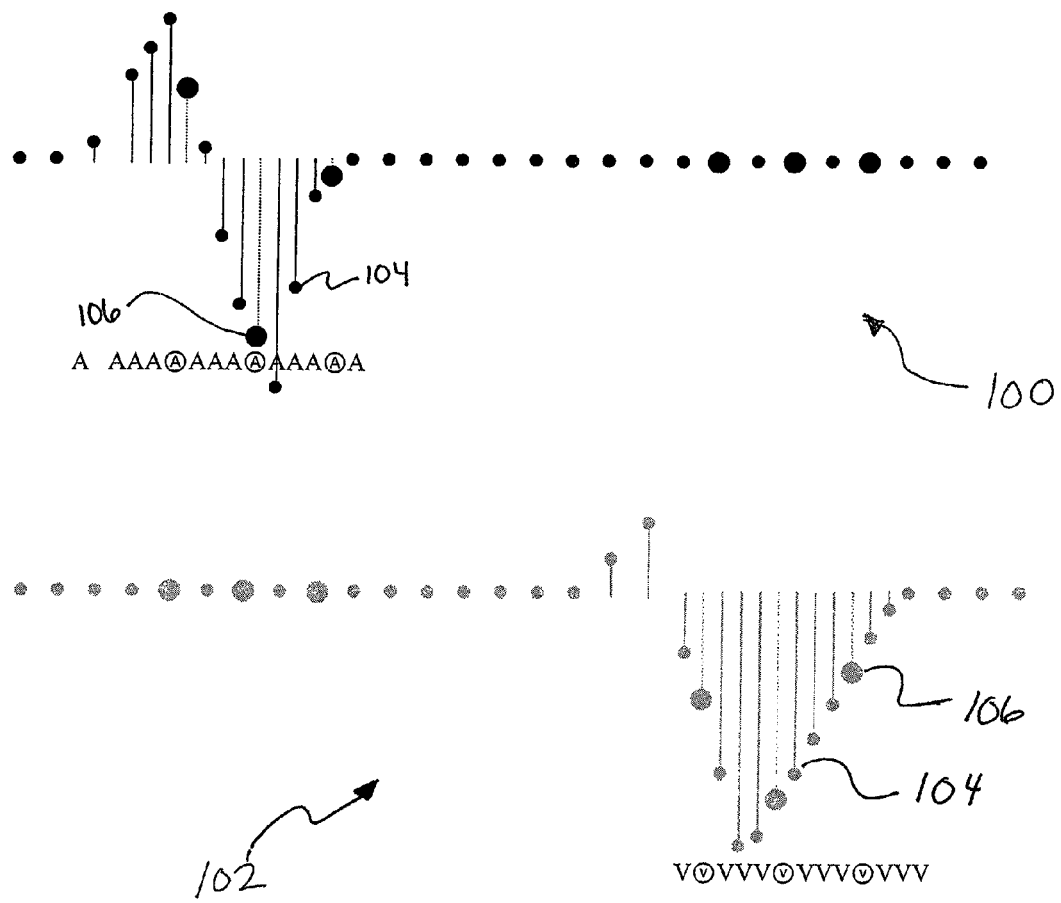
FIG. 7 illustrates a series of exemplary timelines depicting outputs of the gap-fill function circuitry of the system of FIG. 2 based on corresponding inputs to the gap-fill function circuitry of respective signals shown on the timelines of FIG. 5.

The gap-fill function circuitry 42 is powered by the controller 44. For each digital signal passed from an output of the DEMUX 40 to an input, e.g., 42A, of the gap-fill function circuitry 42, such signal is plotted over time with relation to a prior digital signal received from the same input 42A. In turn, gaps between the prior digital signal and the instant digital signal received are subsequently filled. Those skilled in the art would realize there are a wide variety of well-known methods for filling in such signal gaps in the above described fashion (e.g., using curve filling techniques). As such, it should be appreciated that any one of such methods can be applied and still fall within the embodiments of the invention. FIG. 7 illustrates exemplary timelines 100 and 102 showing outputs of the gap-fill function circuitry 42 based on corresponding inputs to the gap-fill function circuitry 42 of respective signals shown on timelines 90 and 92 of FIG. 5. As shown, the gaps are accordingly filled in the above-described manner for each of the sampled signals sent to the gap-fill function circuitry 42 so as to create fully digitized signal representations. As shown in the FIG. 7, each of the sampled signals are referenced as small circles 104, while each of the segments filled in by the gap-fill function circuitry 42 are referenced as large circles 106. This is further shown at the lower footer of each timeline 100, 102, where the samplings are respectively represented by "A" (atrial) and "V" (ventricular) sampling designations. As shown in such lower footer, the designations that are circled represent gap filled segments. Upon filling a gap with respect to one of the sampled signals, the gap filled segment and the digital signal just having been received are transmitted from the system 30 across a corresponding output 34.

Figure 8:
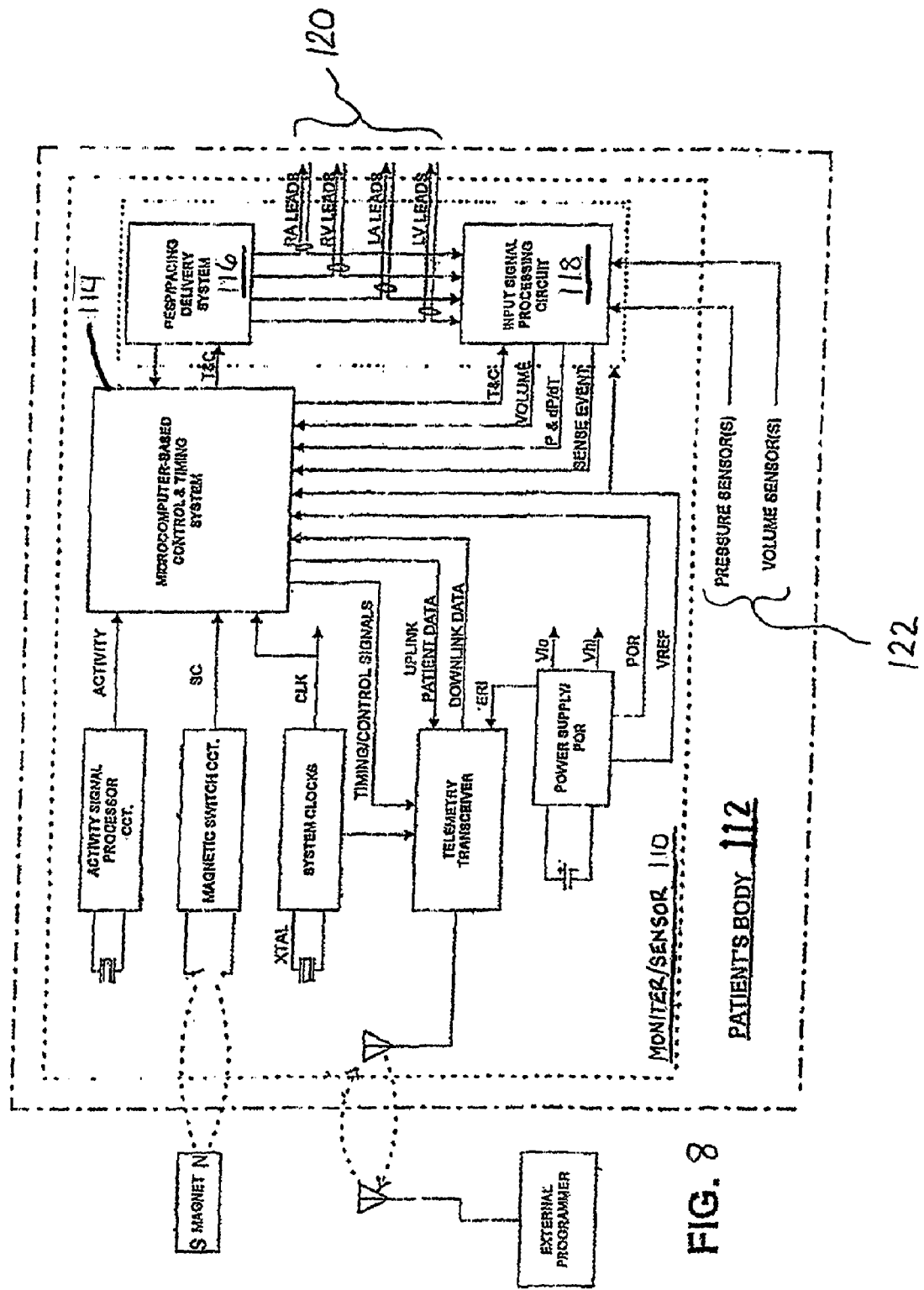
FIG. 8 is a block diagram depicting system architecture from an exemplary multi-chamber monitor/sensor in accordance with embodiments of the invention.

FIG. 8 shows a block diagram depicting system architecture of an exemplary multi-chamber monitor/sensor 110 implanted into a patient's body 112 that provides delivery of a therapy and/or physiologic input signal processing. The typical multi-chamber monitor/sensor 110 has a system architecture that is constructed about a microcomputer-based control and timing system 114 which varies in sophistication and complexity depending upon the type and functional features incorporated therein. The functions of microcomputer-based multi-chamber monitor/sensor control and timing system 114 are controlled by firmware and programmed software algorithms stored in RAM and ROM including PROM and EEPROM and are carried out using a CPU or ALU of a typical microprocessor core architecture. The microcomputer-based multi-chamber monitor/sensor control and timing system 114 may also include a watchdog circuit, a DMA controller, a block mover/reader, a CRC calculator, and other specific logic circuitry coupled together by on-chip data bus, address bus, power, clock, and control signal lines in paths or trees in a manner well known in the art. It will also be understood that control and timing of multi-chamber monitor/sensor 110 can be accomplished with dedicated circuit hardware or state machine logic rather than a programmed micro-computer.

The therapy delivery system 116 can be configured to include circuitry for delivering cardioversion/defibrillation shocks and/or cardiac pacing pulses delivered to the heart or cardiomyostimulation to a skeletal muscle wrapped about the heart. Alternately, the therapy delivery system 116 can be configured as a drug pump for delivering drugs into the heart to alleviate heart failure or to operate an implantable heart assist device or pump implanted in patients awaiting a heart transplant operation.

The input signal processing circuit 118 includes at least one physiologic sensor signal processing channel for sensing and processing a sensor derived signal from a physiologic sensor located in relation to a heart chamber or elsewhere in the body. In certain embodiments, the system 30 of FIG. 2 is included as part of the input signal processing circuit 108; however, the invention should not be limited to such. Instead, it should be appreciated that the system 30 could be positioned in any number of other manners while still falling within the embodiments of the invention. For example, the system 30 could be shown separately as its own block wherein it would be connected between heart leads 120 and/or 122 and the input signal processing circuit 118. In addition, it should be appreciated that certain functionality of the system 30 could be distributed to different components of the multi-chamber monitor/sensor 110 and still fall within the embodiments of the invention. For example, the controller 44 shown in FIG. 2 could have some or all of its functionality incorporated into microcomputer-based control and timing system 104, thereby making the controller 44 expendable.

Figure 9:
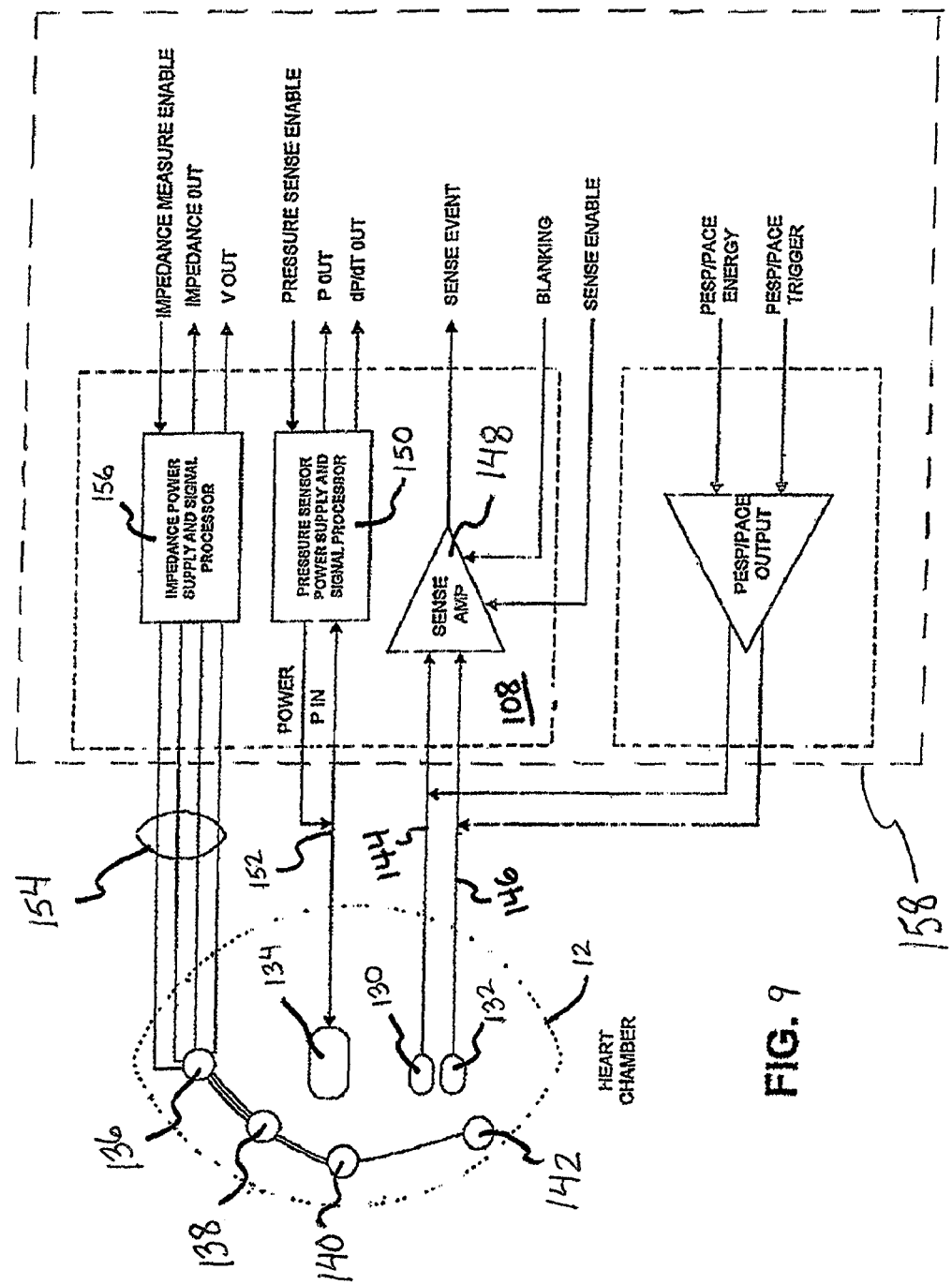
FIG. 9 is a schematic illustration of one pacing, sensing and parameter measuring channel in relation to one heart chamber in accordance with embodiments of the invention.

FIG. 9 schematically illustrates one pacing, sensing and parameter measuring channel in relation to one heart chamber. A pair of pace/sense electrodes 130, 132, a pressure sensor 134, and a plurality, e.g., four, impedance measuring electrodes 136, 138, 140, 142 are located in operative relation to the heart 10.

The pair of pace/sense electrodes 130, 132 are located in operative relation to the heart 10 and coupled through lead conductors 144 and 146, respectively, to the inputs of a sense amplifier 148 located within the input signal processing circuit 118. The sense amplifier 148 is selectively enabled by the presence of a sense enable signal that is provided by a control and timing system (not shown, but similar to what is referenced as 114 in FIG. 8). The sense amplifier 148 is enabled during prescribed times when pacing is either enabled or not enabled in a manner known in the pacing art. The blanking signal is provided by the control and timing system upon delivery of a pacing or PESP pulse or pulse train to disconnect the sense amplifier inputs from the lead conductors 144 and 146 for a short blanking period in a manner well known in the art. The sense amplifier provides a sense event signal signifying the contraction of the heart chamber commencing a heart cycle based upon characteristics of the EGM. The control and timing system responds to non-refractory sense events by restarting an escape interval (EI) timer timing out the EI for the heart chamber, in a manner well known in the pacing art.

The pressure sensor 134 is coupled to a pressure sensor power supply and signal processor 150 within the input signal processing circuit 118 through a set of lead conductors 152. Lead conductors 152 convey power to the pressure sensor 134, and convey sampled blood pressure signals from the pressure sensor 134 to the pressure sensor power supply and signal processor 150. The pressure sensor power supply and signal processor 150 samples the blood pressure impinging upon a transducer surface of the sensor 134 located within the heart chamber when enabled by a pressure sense enable signal from the control and timing system 112. Absolute pressure (P), developed pressure (DP) and pressure rate of change (dP/dt) sample values can be developed by the pressure sensor power supply and signal processor 150 or by the control and timing system for storage and processing.

A variety of hemodynamic parameters may be recorded, for example, including right ventricular (RV) systolic and diastolic pressures (RVSP and RVDP), estimated pulmonary artery diastolic pressure (ePAD), pressure changes with respect to time (dP/dt), heart rate, activity, and temperature. Some parameters may be derived from others, rather than being directly measured. For example, the ePAD parameter may be derived from RV pressures at the moment of pulmonary valve opening, and heart rate may be derived from information in an intracardiac electrogram (EGM) recording.

The set of impedance electrodes 136, 138, 140 and 142 is coupled by a set of conductors 154 and is formed as a lead that is coupled to the impedance power supply and signal processor 156. Impedance-based measurements of cardiac parameters such as stroke volume are known in the art, such as an impedance lead having plural pairs of spaced surface electrodes located within the heart 12. The spaced apart electrodes can also be disposed along impedance leads lodged in cardiac vessels, e.g., the coronary sinus and great vein or attached to the epicardium around the heart chamber. The impedance lead may be combined with the pace/sense and/or pressure sensor bearing lead.

The data stored by medical device 158 may include continuous monitoring of various parameters, for example recording intracardiac EGM data at sampling rates as fast as 256 Hz or faster. In certain embodiments of the invention, an IHM may alternately store summary forms of data that may allow storage of data representing longer periods of time. In one embodiment, hemodynamic pressure parameters may be summarized by storing a number of representative values that describe the hemodynamic parameter over a given storage interval. The mean, median, an upper percentile, and a lower percentile are examples of representative values that may be stored by an IHM to summarize data over an interval of time (e.g., the storage interval). In one embodiment of the invention, a storage interval may contain six minutes of data in a data buffer, which may be summarized by storing a median value, a 94th percentile value (i.e., the upper percentile), and a 6th percentile value (i.e., the lower percentile) for each hemodynamic pressure parameter being monitored. In this manner, the memory of the IHM may be able to provide weekly or monthly (or longer) views of the data stored. The data buffer, for example, may acquire data sampled at a 256 Hz sampling rate over a 6 minute storage interval, and the data buffer may be cleared out after the median, upper percentile, and lower percentile values during that 6 minute period are stored. It should be noted that certain parameters measured by the IHM may be summarized by storing fewer values, for example storing only a mean or median value of such parameters as heart rate, activity level, and temperature, according to certain embodiments of the invention.

Hemodynamic parameters that may be used in accordance with various embodiments of the invention include parameters that are directly measured, such as RVDP and RVSP, as well as parameters that may be derived from other pressure parameters, such as estimated pulmonary artery diastolic pressure (ePAD), rate of pressure change (dP/dt), etc.

In certain embodiments, the system 30 of FIG. 2 is included as part of the input signal processing circuit 108; however, the invention should not be limited to such. Instead, it should be appreciated that the system 30 could be positioned in any number of other manners while still falling within the embodiments of the invention. For example, the system 30 could be shown separately as its own block wherein it would be connected between heart leads 144, 146 and/or 152 and/or 154 and the input signal processing circuit 118. In addition, it should be appreciated that certain functionality of the system 30 could be distributed to different components of the medical device 158 and still fall within the embodiments of the invention. For example, the controller 44 shown in FIG. 2 could have some or all of its functionality incorporated into the mentioned microcomputer-based control and timing system, thereby making the controller 44 expendable.

Figure 10:
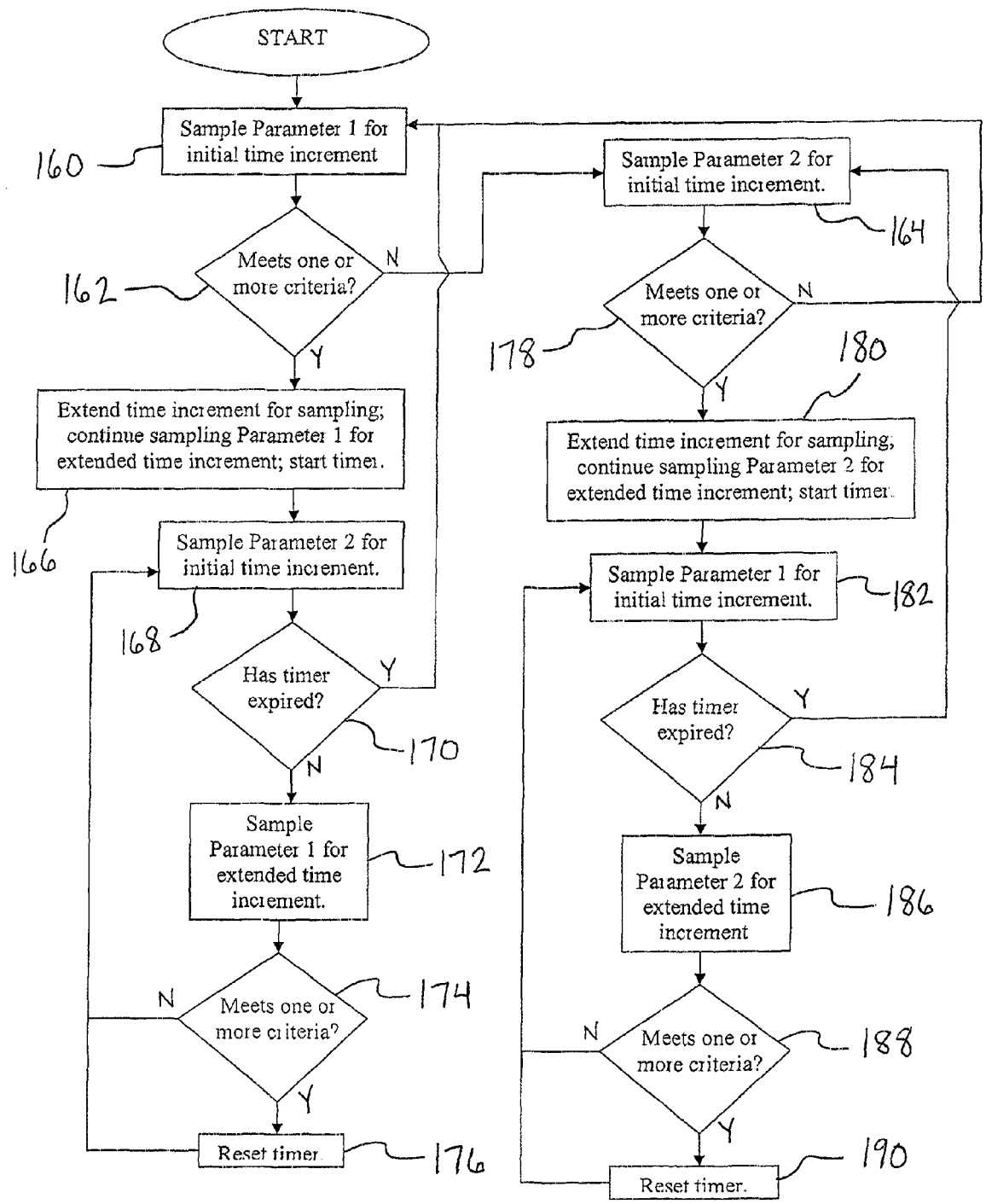
FIG. 10 is a flowchart of a method of using the system of FIG. 2 in accordance with certain embodiments of the invention.

FIG. 10 is a flowchart of a method of using the system of FIG. 2 in accordance with certain embodiments of the invention. As such, reference is made below to the elements used in FIG. 2. The method can be performed by any medical device used for monitoring the condition and/or status of a patient, and in certain embodiments, such medical device may be used for cardiac parameter monitoring purposes. The method is limited in only showing steps of how the system 30 alternately samples the signals (corresponding to parameters of a patient) and subsequently modifies the switching rates of the MUX 36, and in turn, the sampling ratios of the signals if one of the signals meets the one or more criteria, as described above. It should be appreciated that once these switching rates, and in turn, sampling ratios are established, the sampled signals will proceed through the ADC 38, the DEMUX 40, and the gap-fill function circuitry 42 as already described above. The system of the invention, as exemplified with respect to FIG. 2, is adapted to monitor a plurality of channels, and in turn, is adapted to sample each of the signals carried on such channels. However, in order to simplify the flowchart for the reader, only two input channels, and in turn, only two corresponding signals are detailed. By illustrating the method with respect to two input channels, it should be apparent how the method as well as the corresponding flowchart of FIG. 10 would vary with more input channels being utilized.

The method starts at an initial stage, during which there is a monitoring of the parameters of a patient by use of one or more sensors of a medical device (e.g., as illustrated in FIG. 1), where such parameters are each respectively delivered to input channels 32 of the system 30. Step 160 involves initially monitoring one input channel, e.g., 32A, of the system 30 and in turn, sampling the corresponding signal or parameter of the patient (as shown, Parameter 1) carried across such channel via the MUX 36. In this step, as discussed above, the MUX 36 would initially operate at a switching rate that is used in "normal mode" of operation of the system 30, whereby the sampling of each of the parameters would be for an initial time increment.

Step 162 involves a determination by the event detector 46 as to whether the sampled parameter meets one or more criteria, as described above. If the sampled parameter does not meet the one or more criteria, the MUX 36, in step 164, switches to the other input channel, e.g., 32B of the system 30 and samples the corresponding parameter of the patient (as shown, Parameter 2) carried across such channel. However, if the sampled parameter meets one or more criteria, as described above, a signal is sent to controller 44 and in turn, controller 44 designates such parameter as high priority and switches the operation of the system 30 to a "high priority mode". In turn, in step 166, the sampling increment for Parameter 1 is extended beyond that of the initial time increment and Parameter 1 is continually sampled during such extended time increment. As mentioned above, in certain embodiments, the system 30 remains in such "high priority mode" for a preset time duration. In certain embodiments, this preset duration can be provided by a timer incorporated in the controller 44. As such, such timer is started in step 166 as well.

In certain embodiments, as described above, the MUX 36 may still continue to sample signals from the different channels during "high priority mode". As such, following step 166, the MUX 36, in step 168, switches to the other input channel, e.g., 32B of the system 30, and samples the corresponding parameter of the patient (as shown, Parameter 2) carried across such channel. In certain embodiments, as described above, the sampling ratio between the signals carried on the high priority input channel and the other channels would be N:1. As such, Parameter 2 would be sampled in step 168 for the initial time increment, and subsequently, MUX 36 would switch back to the high priority channel.

In certain embodiments, following each sampling cycle of the input channels, the timer is checked to see if the preset duration is over. This is shown in step 170. If the timer has not expired, the MUX 36 would continue to sample Parameter 1 for the extended time increment as referenced by step 172. Step 174, like step 162 above, again involves a determination by the event detector 46 as to whether the sampled parameter meets one or more criteria. If the sampled parameter does not meet the one or more criteria, the flowchart loops back to step 168, wherein the MUX 36 switches to the other input channel 32B, sampling Parameter 2 for initial time increment. However, if the sampled parameter meets the one or more criteria in step 174, it provides an indication that the event is still not over with respect to Parameter 1. As such, the timer is reset in step 176 so as to extend the time period over which the high priority input channel 32A has extended sampling. Subsequently, the flowchart loops back to step 168, wherein the MUX 36 switches to the other input channel 32B, sampling Parameter 2 for initial time increment.

Conversely, if the timer, checked in step 170, has expired, the system 30 will revert back to "normal mode" operation. In turn, the flowchart loops back to step 160, where Parameter 1 is sampled for the initial time increment.

As should be appreciated, the series of steps performed after Parameter 1 is sampled by the MUX for the initial time increment in step 160 is similar with respect to Parameter 2 upon sampling of Parameter 2 for the initial time increment by MUX in step 174. In particular, steps 162 and 166-176 with respect to Parameter 1 are the same as steps 178-190 with respect to Parameter 2, except for the Parameter 1 and Parameter 2 being switched in the steps. As such, description of the steps will not be further detailed.

It will be appreciated the embodiments of the present invention can take many forms. The true essence and spirit of these embodiments of the invention are defined in the appended claims, and it is not intended the embodiment of the invention presented herein should limit the scope thereof.

The invention claimed is:

1. A medical device for monitoring patient comprising:
   a plurality of sensors operatively connected to a medical device and implantable within a patient for monitoring patient parameters;
   an analog-to-digital converter (ADC) located within the medical device; and
   a switching device at least partially located within the medical device and configured to operate in one of a first and a second mode, the switching device separately connecting the ADC to each sensor of the plurality of sensors at least once to complete a switching cycle, the switching device connecting the ADC to each sensor for an initial time increment in each switching cycle when operating in the first mode, the switching device connecting the ADC to a selected one of the sensors for an extended time increment with respect to the other sensors in each switching cycle when operating in the second mode, the extended time increment being longer than the initial time increment.

2. The medical device of claim 1, wherein the medical device includes a medical monitoring device.

3. The medical device of claim 2, wherein the plurality of sensors includes a plurality of one or more of a sense/pace electrode, a blood pressure sensor, an accelerometer, an impedance electrode, a flow probe, a microphone, a sonometric crystal, a metabolic or chemical sensor, and an electrical and/or mechanical sensor.

4. The medical device of claim 1, further comprising an event detector electrically connected to the first switching device so as to monitor the sampled signals both during the first and second operation modes, and wherein presence of an event across one of the sampled signals switches operation of the first switching device from the first mode to the second mode.

5. A computer-readable medium programmed with instructions for monitoring the condition or status of a patient, the medium comprising instructions for causing a programmable processor to:

separately sample parameters of a patient from a plurality of sensors implanted within the patient, each parameter being sampled at least once to complete a switching cycle, the parameters being sampled in a first mode or a second mode, the parameters sampled an equal number of times in each switching cycle in the first mode, a selected one of the parameters being sampled more times than the other parameters in each switching cycle in the second mode;

analyze each sampled parameter to determine whether such sampled parameter meets one or more criteria, the selected one of the parameters being the sampled parameter meeting the one or more criteria; and switch sampling of the parameters from the first mode to the second mode if one of the parameters meets the one or more criteria.

6. The computer-readable medium of claim 5, wherein each parameter sampling occurs over an initial time increment in each switching cycle in the first mode.

7. The computer-readable medium of claim 5, wherein sampling of the selected one of the parameters occurs over an extended time increment in each switching cycle in the second mode, the extended time increment being longer than the initial time increment.

8. The computer-readable medium of claim 5, further comprising instructions to convert each sampled parameter to a stream of data points representing such sampled parameter, the stream of data points for the selected one of the parameters having gaps between adjacent data points corresponding to points in time when the other parameters were being sampled.

9. The computer-readable medium of claim 8, further comprising instructions to fill the gaps with calculated data points based on values of at least some of the stream of data points for the selected one of the parameters.

10. The computer-readable medium of claim 5, further comprising instructions to fill a gap in the sampled parameters through use of gap-fill function circuitry.

11. The computer-readable medium of claim 5, wherein the parameters include cardiac parameters, the plurality of sensors being positioned proximate to a heart of the patient.

12. The computer-readable medium of claim 5, wherein each parameter sampling occurs through use of a multiplexor, wherein the multiplexor switches from the first mode to the second mode via a controller, and wherein the controller switches from the multiplexor from the second mode back to the first mode after a duration of time from when the one parameter met the one or more criteria.

13. The computer-readable medium of claim 5, wherein the sampling during switching cycles in the second mode involves a sampling ratio N:1 between the one parameter and the other parameters, with N being greater than one.

14. The computer-readable medium of claim 5, wherein the one or more criteria include a threshold, the one or more criteria being met when the one parameter extends to or beyond the threshold.

15. The computer-readable medium of claim 14, wherein the comparison of the parameters to the one or more criteria involves use of an event detector.

16. The computer-readable medium of claim 5, further comprising an instruction to transmit each sampled signal to an analog-to-digital converter in order to digitize each sampled signal.

17. A medical device for monitoring the condition or status of a patient, comprising:

a plurality of sensors operatively coupled to a medical device and implanted within a patient for monitoring patient parameters; and circuitry at least partially housed within the medical device, including first and second switching devices, and adapted to operate in first and second modes, the first and second switching devices separately connecting to each sensor of the plurality of sensors at least once to complete a switching cycle, the connections to each sensor over the switching cycle occurring for an initial time increment during circuitry operation in the first mode, and the connections to a selected one of the plurality of sensors occurring for an extended time increment during circuitry operation in the second mode, the extended time increment being longer than the initial time increment.

18. The medical device of claim 17, wherein the selected one sensor corresponds to one of the parameters, and wherein the one parameter meeting one or more criteria prompts switching of the circuitry from the first mode to the second mode.

* * * * *